United States Patent [19]

Van Sorge

[11] 3,972,828
[45] Aug. 3, 1976

[54] CATALYST COMPRISING MAGNESIUM OXIDE AND A CELLULOSIC POLYMERIC BINDER

[75] Inventor: Bernardus J. Van Sorge, Selkirk, N.Y.

[73] Assignee: General Electric Company, Pittsfield, Mass.

[22] Filed: July 12, 1974

[21] Appl. No.: 487,923

Related U.S. Application Data

[62] Division of Ser. No. 846,925, Aug. 1, 1969, Pat. No. 3,843,606.

[52] U.S. Cl. ............................................... 252/430
[51] Int. Cl.² ........................................... B01J 31/02
[58] Field of Search .................................... 252/430

[56] References Cited
UNITED STATES PATENTS

| | | | |
|---|---|---|---|
| 3,006,866 | 11/1961 | Corte et al. | 260/624 C X |
| 3,446,856 | 5/1969 | Hamilton | 260/621 X |
| 3,683,030 | 8/1972 | Sparks | 252/430 X |
| 3,843,606 | 11/1974 | Van Sorge | 252/430 |
| 3,850,845 | 11/1974 | Vickery | 252/430 |

FOREIGN PATENTS OR APPLICATIONS

| | | | |
|---|---|---|---|
| 717,588 | 11/1954 | United Kingdom | 260/621 R |

*Primary Examiner*—Patrick P. Garvin
*Assistant Examiner*—John P. Sheehan
*Attorney, Agent, or Firm*—William F. Mufatti; Edward A. Hedman

[57] ABSTRACT

This invention is for a shaped, alkylation catalyst comprising magnesium oxide bonded with an inert, organic polymeric binder and to the use of the catalyst in a process for the ortho-alkylation of phenols. The process comprises the vapor phase reaction of a non-ortho-substituted phenol with an alcohol in the presence of the catalyst. The catalyst of the invention is an improvement over prior art catalysts used for ortho-alkylation of phenols as it substantially reduces the induction period for maximum reaction selectivity, eliminates loss of catalyst arising with use of powders and substantially extends catalyst life.

6 Claims, No Drawings

CATALYST COMPRISING MAGNESIUM OXIDE AND A CELLULOSIC POLYMERIC BINDER

This is a division of application Ser. No. 846,925, filed Aug. 1, 1969, now U.S. Pat. No. 3,843,606.

BACKGROUND OF THE INVENTION

1. Introduction

This invention relates to the ortho-alkylation of phenols, and more particularly, to the vapor-phase ortho-alkylation of phenols by reaction of a non-ortho-alkylated phenol with an alcohol in the presence of a shaped catalyst comprising magnesium oxide bonded with an inert, organic polymeric binder.

2. Description of the Prior Art

In commonly assigned Hamilton U.S. patent application Ser. No. 371,189, filed May 29, 1964, now abandoned there is disclosed and claimed a method for methylating the ortho positions of phenol by the vapor phase reaction of a phenol with methanol in the presence of magnesium oxide as a catalyst at a catalyst bed temperature in the range of 475° to 600° C. Under the conditions described in the Hamilton application, phenol is selectively ortho-methylated in yields in excess of 95%. Thus, the reaction offers a means for economically converting phenol to ortho-cresol, a useful disinfectant and wood preservative, and for converting both phenol and ortho-cresol to 2,6-xylenol, a monomer which can be polymerized to form poly-2,6-xylenol, a high performance thermoplastic material.

While the Hamilton invention provides an economic synthesis for both 2,6-xylenol and ortho-cresol from phenol, the service life of the magnesium oxide catalyst is relatively short due to the high temperature at which the reaction is required to take place, i.e. about 90 to 100 hours' service life at the typical reaction temperature of about 530°C. Also the magnesium oxide catalyst of the Hamilton application is only moderately selective with respect to methanol, with methanol selectivity being in the range of about 40 to 50 percent. This means that more than about two moles of methanol are required for each mole of phenol entering into reaction with the methanol. In addition, use of unmodified magnesium oxide in powdered form results in a rather large induction period for maximum selectivity. The term "induction period" may be defined as the period from the time of starting the reaction to the time at which the catalyst reaches and maintains maximum ortho-alkylation selectivity. Finally, the use of magnesium oxide in powdered or sintered form provides processing difficulties.

STATEMENT OF THE INVENTION

The present invention is predicated upon the discovery that if the ortho-alkylation catalyst consists of magnesium oxide bonded with an inert, organic polymeric binder, the alkylation reaction will proceed with a high degree of both methanol and phenol selectivity and the induction period for maximum selectivity is substantially reduced. Moreover, the catalyst may be molded to a desired shape and will have strength properties that will prevent particles of the catalyst from breaking or flaking off in operation or handling thereby substantially extending the service life of the catalyst with a minimum of loss during operation. In addition, the reaction temperature may be reduced thereby improving the overall economy of the process.

Accordingly, the present invention has as one object, the provision of a catalyst which will enable ortho-alkylation of phenol to be carried out with a high degree of selectivity and high yield.

Another object of the invention is to provide a magnesium oxide catalyst having excellent physical strength properties which may be molded to a desired shape and which will have a service life of many hundreds of hours before needing regeneration or other treatment.

Still another object is to provide a process for formation of ortho-alkylated phenols in high yield.

DESCRIPTION OF THE PREFERRED EMBODIMENTS

In one aspect, the ortho-alkylation catalyst of the invention is provided by blending finely divided magnesium oxide powders with finely divided polymer powders or by wetting the magnesium oxide powder with a solution of the polymer in a suitable solvent. Where polymer powders are used, both the polymer powders and magnesium oxide powders are preferably maintained below an average particle size of 500 microns in diameter. The percentage of polymer in the blend is preferably maintained low and may be as little as 1% by weight or as high as 15% or more. The preferred range varies from 2 to 6% by weight. After the powders are blended together, water is added to the blend in an amount sufficient to completely wet the blend so that it may be molded to shape. Typically, one part by weight water is added for each part of the powder blend. The blend is then molded to shape under pressure and dried at about 200°F. and subsequently calcined at an elevated temperature. The calcination temperature should be below that temperature which causes a visible degradation of the polymer binder and should be maintained at this temperature for a time sufficient to dry the catalyst. In general, a calcination temperature of between 300° and 500°F. for a time up to about 3 hours is sufficient. As water is evaporated from the catalyst, minute pores form thereby exposing the magnesium oxide and making the catalyst active. A surface area of at least 20, and preferably from 130 to 200 square meters per gram of catalyst is desirable. The shape of the catalyst may be in the form of Raschig rings, cylinders, tablets or any other shape known to the art.

The polymeric binder is not critical provided it is inert to the reactants, is not affected by the solvents in the reaction system and is capable of withstanding the elevated temperatures of the reaction, though some coking of the binder is permissible and may even be desirable. The cellulosic molding compounds such as cellulose acetate, cellulose propionate and cellulose acetate butyrate are preferred. Other polymers that are suitable, but less preferred include the acetyl resins, the epoxy resins, the polyphenylene ethers, the melamine-formaldehyde molding compounds, the phenol-formaldehyde and phenol-furfural molding compounds, the polyester and alkyl molding compounds, and the urea-formaldehyde molding compounds. Other suitable organic plastic binders would be obvious to those skilled in the art.

The method for forming the ortho-alkylated phenols comprises a vapor-phase reaction of an alkyl alcohol and a nonortho-substituted phenol in the presence of the catalyst of this invention at a catalyst temperature of at least 460° C. and preferably at a temperature varying between 460° C. and 600° C. In general, the process is equivalent to the process disclosed in the above-noted Hamilton patent application Ser. No. 371,189 and differs therefrom by the substitution of the catalyst of this invention.

While the invention has been described as applying specifically to phenol and ortho-cresol, it applies in general to phenols having an ortho-hydrogen. For example, it also applies to ortho-phenyl phenol, ortho-ethyl phenol, and to phenols in which there are alkyl and aryl groups in the meta and para positions. These phenols may be represented by the formula

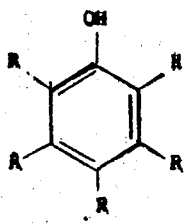

in which each R is a monovalent substituent selected from the group consisting of hydrogen, alkyl, phenyl, and alkyl-substituted phenyl.

The magnesium oxide used as catalyst in conjunction with the inert plastic binder is a material having a very high surface to weight ratio. Magnesium oxides having the desired porosity may be prepared by thermally decomposing magnesium carbonate, basic magnesium carbonate, and magnesium hydroxide as these materials may be converted to magnesium oxide without fusing or sintering.

In carrying out an alkylation in accordance with this invention, any one or a mixture of phenols having an ortho-hydrogen may be vaporized and passed through a reactor heated to a temperature of at least 460° C. containing the magnesium oxide catalyst of the invention. In order to obtain the maximum yield or ortho-alkylated products, at least one mole of an alkyl alcohol and preferably from one to three moles of the alcohol is used for each ortho position in the phenol to be alkylated. For example, if phenol which has 2-ortho-hydrogens per molecule is to be methylated to produce a maximum yield of 2,6-xylenol, it is desirable to use two to six moles of methanol for each mole of phenol with higher yields being obtained with the higher ratios of methanol to phenol.

The vapors issuing from the reactor are condensed and the products separated by conventional methods such as crystallization, distillation, etc. The reaction proceeds at atmospheric pressure, but it is obvious that pressures above or below may be used.

The selectivity favoring ortho-alkylation over meta or para alkylation under steady state condition, is substantially the same for the magnesium oxide catalyst of the invention as for pure magnesium oxide. One advantage to operating with the catalyst of this invention lies in the fact that the life of the catalyst is extended considerably before regeneration or other treatment is needed. Catalysts made according to this invention have operated without reduction in catalystic activity for periods in excess of 500 hours.

An additional major benefit accruing to the magnesium oxide catalyst of the invention lies in the reduction of the induction period that is encountered with other magnesium oxide catalysts. As noted above, the induction period is the time necessary for a catalyst to reach maximum selectivity for ortho-alkylation. During this induction period, the prior art catalysts usually produce a relatively large amount of by-products such as 2,4,6-mesitol and the like. The catalyst of the subject invention results in a molar phenol selectivity reaching a level of over 95% and a molar methanol selectivity in excess of 65% in approximately 6 hours at a temperature of about 480° C. as compared to about 24 hours and more for catalysts of the prior art.

In the following Example 1, the system consisted of a reservoir containing a solution of methanol and phenol connected to a metering pump which fed the reactants through a ¼ inch stainless steel tube into a vertical vaporizer made from a 12-inch long piece of 1″ O.D., 0.8″ I.D. stainless steel tubing. The vaporizer was partially immersed in a bath of fused salt to a depth of about 6 inches. The vapors from the reactor were fed to a 0.8″ I.D. stainless steel tube reactor through a 1 inch length of ¼ inch I.D. stainless steel pipe located 5½ inches above the bottom of the vaporizer and connected to the reactor 13″ from its bottom. The reactor was 24″ long and was immersed in the fused salt bath to a depth of 14 inches. Since the inlet tube of the reactor coming from the vaporizer also passed through the fused salt bath, it served as a preheater for the vapor issuing from the vaporizer to bring the vapor up to the temperature of the reactor. The reactor was equipped with a thermowell made from ⅛ inch stainless steel tubing concentrically located in the reactor and extending downward into the catalyst bed to a depth of 1 to 6 inches. Thus, the catalyst bed temperature could be measured throughout a large section of the tube. The reactor tube was filled with a constant volume of 100 milliliters of catalyst which filled the tube to a depth of about 12 inches. Thus the vapors were fed to the top of the catalyst bed in the reactor and product vapors left the reactor through a ⅜″ O.D. stainless steel tube connected to the bottom of the reactor. The product vapors from the reactor were led to a water-cooled condenser and receiver.

The catalyst used was prepared by blending 200 grams of commercial magnesium oxide catalyst with about 10 grams of Avicel polymer, a cellulosic polymer available from the FMC company and about 200 grams of water. The blend was molded into cylindrically shaped pellets having a diameter and length of 3/16 inch. The catalyst was dried at 200°F. and calcined by heating to further dryness at about 450° F. for about 3 hours. The catalyst was then placed in a reaction chamber which was maintained at a temperature of 480° C. The feed composition was vaporized and the vapors passed through the catalyst chamber. The conditions and results are indicated in the following table:

TABLE I

| Feed Composition | Example 1 |
|---|---|
| Molar Ratio Methanol to Phenol | 6:1 |
| Wt. % Water in Feed | 6 |
| Operating Conditions | |
| Temperature (°C.) | 482 |
| LHSV (hr⁻¹)* | 1.52 |
| Pressure (psig) | 0 |
| Phenolin Distribution (wt.%) | |
| 0-cresol | 26.6 |
| 2,6-xylsnol | 60.8 |
| 2,4,6-mesitol | 1.5 |

TABLE I-continued

| | |
|---|---|
| Phenol | 11.3 |

*LHSV is the liquid hourly space velocity and defines the volume of liquid per volume of catalyst per hour.

From the above table, it can be seen that the alkylation which took place was primarily occurring in the ortho-position. The ortho-cresol formed in the reaction and unreacted phenol may be recycled if desired. By increasing the liquid hourly spaced velocity, the ratio of ortho-cresol to 2,6-xylenol may be substantially increased. For example, using substantially the same reaction conditions, an increase in the liquid hourly space velocity to 3.47 hr.$^{-1}$ would result in a phenolic distribution comprising about 42.7% unreacted phenol, 36.2% ortho-cresol, 20.2% 2,6-xylenol, and about 0.8% 2,4,6-mesitol.

In the following Examples 2 and 3, the procedure of Example 1 is repeated. In Example 2, the catalyst used was substantially the same as that of Example 1. In Example 3, the catalyst used was prepared by pelletizing and calcining substantially pure powders of magnesium oxide at a temperature of about 500° F. The conditions and results are indicated in the following Table II:

TABLE II

| Feed Composition | Example 2 | Example 3 |
|---|---|---|
| Molar ratio Methanol to Phenol | 6:1 | 6:1 |
| Wt.% Water in Feed | 10 | 12.4 |
| Operating Conditions | | |
| Temperature (°C.) | 489 | 504 |
| LHSV (hr.$^{-1}$) | 1.83 | 1.65 |
| Pressure (psig) | 0 | 0 |
| Results | | |
| Induction Period (hrs.) | 8 | 23.5 |
| Molar Phenol Selectivity[1] | 93.7 | 89.5 |
| Molar Methanol Selectivity[2] | 72.5 | 59.5 |
| Production Rate (lbs. 2,6-xylenol/hr./ft. catalyst) | 19.3 | 14.0 |

[1] The molar phenol selectivity is defined as the ratio of phenol converted to 2,6-xylenol to phenol converted to 2,6-xylenol and by-products multiplied by 100. The amount of phenol converted to ortho-cresol is not included in the definition as it is recycled in the feed stream if desired.
[2] The molar methanol selectivity is defined as the ratio of methanol reacted to form 2,6-xylenol to the methanol reacted to form 2,6-xylenol and other by-products multiplied by 100. The amount of methanol converted to ortho-cresol is not included in the definition as it is recycled in the feed stream if desired.

From the above Table, it can be seen that the induction period for the reaction using the catalyst of this invention is substantially shorter than that for the prior art magnesium oxide catalyst. Moreover, methanol selectivity is substantially improved. A catalyst such as that of Example 2 would have a total life of 500 hours or more while that of Example 3 would have a total life of less than 100 hours.

While the foregoing discloses certain specific embodiments of the invention, it is understood that there are many modifications which obviously fall within the proper scope of the invention. Accordingly, the invention is intended to be limited in scope only as may be necessitated by the scope of the appended claims.

I claim:

1. A porous catalyst comprising a mixture of magnesium oxide bonded with from 1–15% by weight of an inert, organic cellulosic polymeric binder, the catalyst having a surface area of at least 20 square meters per gram.

2. The catalyst of claim 1 where the inert, organic polymeric binder constitutes from 2 to 6% by weight of the catalyst.

3. The catalyst of claim 1 in the shape of pellets.

4. The catalyst of claim 1 in the shape of Raschig rings.

5. A process for preparing a catalyst for the ortho-alkylation of phenols comprising blending a mixture of magnesium oxide and from 1–15% by weight of an inert organic cellulosic binder with about an equal amount of water, molding the blend to shape, and heating at an elevated temperature below the degradation temperature of the cellulosic binder until dry.

6. The process of claim 5 where the elevated temperature is ultimately at least 300°F.

* * * * *

UNITED STATES PATENT AND TRADEMARK OFFICE
CERTIFICATE OF CORRECTION

PATENT NO. : 3,972,828
DATED : August 3, 1976
INVENTOR(S) : Bernardus J. Van Sorge It is certified that error appears in the above-identified patent and that said Letters Patent are hereby corrected as shown below:

Col. 5, line 2, "11.3" should be --11.1--

Signed and Sealed this twenty-third Day of August 1977

[SEAL]

Attest:

RUTH C. MASON
*Attesting Officer*

C. MARSHALL DANN
*Commissioner of Patents and Trademarks*